US007172633B2

(12) United States Patent
Samain et al.

(10) Patent No.: US 7,172,633 B2
(45) Date of Patent: Feb. 6, 2007

(54) LIGHTENING DYE COMPOSITION COMPRISING AT LEAST ONE CATIONIC DIRECT DYE CONTAINING MIXED CHROMOPHORES

(75) Inventors: Henri Samain, Bievres (FR); Leila Hercouet, Chelles (FR)

(73) Assignee: L'Oréal S.A., Paris (FR)

( * ) Notice: Subject to any disclaimer, the term of this patent is extended or adjusted under 35 U.S.C. 154(b) by 331 days.

(21) Appl. No.: 10/980,899

(22) Filed: Jun. 16, 2004

(65) Prior Publication Data
US 2005/0183211 A1    Aug. 25, 2005

Related U.S. Application Data

(60) Provisional application No. 60/499,336, filed on Sep. 3, 2003.

(30) Foreign Application Priority Data
Jun. 16, 2003  (FR) ................... 03 07186

(51) Int. Cl.
*A61K 7/13*  (2006.01)
(52) U.S. Cl. ...................... 8/405; 8/406; 8/407; 8/410; 8/411; 8/423; 8/426; 8/437; 8/565; 8/566; 8/567; 8/568; 8/570; 8/573; 8/574; 534/573; 534/608; 548/269.4; 548/301.7
(58) Field of Classification Search .............. 8/405, 8/406, 407, 410, 411, 423, 426, 437, 565, 8/566, 567, 568, 570, 573, 574; 534/573, 534/608; 548/269.4, 301.7
See application file for complete search history.

(56) References Cited

U.S. PATENT DOCUMENTS

| | | | |
|---|---|---|---|
| 3,100,739 A | 8/1963 | Kaiser et al. | |
| 3,524,842 A | 8/1970 | Grossman et al. | |
| 3,578,386 A | 5/1971 | Kalopissis et al. | |
| 3,617,163 A | 11/1971 | Kalopissis et al. | |
| 3,817,698 A | 6/1974 | Kalopissis et al. | |
| 3,867,456 A | 2/1975 | Kalopissis et al. | |
| 3,955,918 A | 5/1976 | Lang | |
| 4,025,301 A | 5/1977 | Lang | |
| 4,226,784 A | 10/1980 | Kalopissis et al. | |
| 4,823,985 A | 4/1989 | Grollier et al. | |
| 4,886,517 A | 12/1989 | Bugaut et al. | |
| 5,708,151 A * | 1/1998 | Mockli ........................ | 534/608 |
| 5,879,413 A | 3/1999 | Pengilly et al. | |
| 5,888,252 A | 3/1999 | Mockli | |
| 5,919,273 A | 7/1999 | Rondeau et al. | |
| 5,980,587 A | 11/1999 | Samain | |
| 5,993,490 A | 11/1999 | Rondeau et al. | |
| 6,045,591 A | 4/2000 | Deneulenaere | |
| 6,136,042 A | 10/2000 | Maubru | |
| 6,179,881 B1 | 1/2001 | Henrion et al. | |
| 6,297,362 B1 | 10/2001 | Kunde et al. | |
| 6,368,360 B2 | 4/2002 | Samain | |
| 6,416,770 B1 | 7/2002 | Leduc et al. | |
| 6,458,167 B1 | 10/2002 | Genet et al. | |
| 6,530,959 B1 | 3/2003 | Lang et al. | |
| 6,797,013 B1 | 9/2004 | Cotteret et al. | |
| 6,863,883 B1 | 3/2005 | Tsujino et al. | |
| 6,884,265 B2 | 4/2005 | Vidal et al. | |
| 2001/0001333 A1 | 5/2001 | Samain | |
| 2001/0044975 A1 | 11/2001 | Matsunaga et al. | |
| 2003/0066143 A1 | 4/2003 | Mockli | |
| 2005/0039268 A1 | 2/2005 | Plos et al. | |

FOREIGN PATENT DOCUMENTS

| | | |
|---|---|---|
| DE | 25 27 638 | 5/1976 |
| DE | 25 38 363 | 5/1976 |
| DE | 33 35 956 | 4/1985 |
| DE | 41 37 005 | 5/1993 |
| DE | 42 20 388 | 12/1993 |
| DE | 198 45 640 | 4/2000 |
| EP | 0 318 294 | 5/1989 |
| EP | 0 714 954 | 6/1996 |
| EP | 0 810 851 | 12/1997 |
| EP | 0 850 636 | 7/1998 |
| EP | 0 850 637 | 7/1998 |
| EP | 0 860 636 | 8/1998 |
| EP | 0 918 053 | 5/1999 |
| EP | 0 920 856 | 6/1999 |
| EP | 1 062 940 | 12/2000 |

(Continued)

OTHER PUBLICATIONS

STIC Search Report Jun. 23, 2006.*
Co-pending U.S. Appl. No. 10/980,899 to Henri Samain et al., filed Jun. 16, 2004.
French Search Report for French Application No. 03 07185 (Priority Application for U.S. Appl. No. 10/980,900) dated Mar. 15, 2004, Examiner Irwin.
French Search Report for French Appl. No. 03 07186 (Priority Application for U.S. Appl. No. 10/980,899) dated Mar. 11, 2004, Examiner Vayssié.
Seidler et al., "The qualification of different ditetrazolium salts as indicators in the oxido-reductase historchemistry," Acta Histochem. vol. 61(1), pp. 48-52 (1978).

(Continued)

*Primary Examiner*—Eisa Elhilo
(74) *Attorney, Agent, or Firm*—Finnegan, Henderson, Farabow, Garrett & Dunner, L.L.P.

(57) ABSTRACT

The present invention relates to a lightening dye composition comprising, in a suitable dyeing medium, an oxidizing agent, an alkaline agent in an amount such that the pH of the composition is greater than 7, and a mixed cationic dye comprising several chromophores linked together via a linker, at least two of the chromophores being different, the chromophores having an absorbance of between 400 and 800 nm. The invention makes it possible to obtain particularly fast colorations.

39 Claims, No Drawings

FOREIGN PATENT DOCUMENTS

| | | |
|---|---|---|
| EP | 1 133 975 | 9/2001 |
| EP | 1 133 976 | 9/2001 |
| FR | 1 221 122 | 5/1960 |
| FR | 1 516 943 | 3/1968 |
| FR | 1 540 423 | 9/1968 |
| FR | 1 560 664 | 3/1969 |
| FR | 1 567 219 | 5/1969 |
| FR | 2 189 006 | 1/1974 |
| FR | 2 275 462 | 1/1976 |
| FR | 2 285 851 | 4/1976 |
| FR | 2 570 946 | 4/1986 |
| FR | 2 586 913 | 3/1987 |
| FR | 2 757 385 | 6/1998 |
| FR | 2 788 433 | 7/2000 |
| FR | 2 825 625 | 12/2002 |
| GB | 0 738 585 | 10/1955 |
| GB | 1 163 385 | 9/1969 |
| GB | 1 195 386 | 6/1970 |
| GB | 1 491 930 | 11/1977 |
| GB | 1 514 466 | 6/1978 |
| WO | WO 95/01772 | 1/1995 |
| WO | WO 95/15144 | 6/1995 |
| WO | WO 97/44004 | 11/1997 |
| WO | WO 99/48465 | 9/1999 |
| WO | WO 01/66646 | 9/2001 |
| WO | WO 02/30374 | 4/2002 |
| WO | WO 02/078596 | 10/2002 |
| WO | WO 03/006554 | 1/2003 |
| WO | WO 03/018021 | 3/2003 |
| WO | WO 03/029359 | 4/2003 |
| WO | WO 03/030909 | 4/2003 |

OTHER PUBLICATIONS

Alberti et al., "Cationic Dyes for Acrylic Fibres v. Cationic Dyes Derived From Several Heterocyclic Amines With Two or more Heteroatoms," Ann. Chim (Rome) vol. 65(Nos. 5-6), pp. 305-314 (1975).

Alberti et al., "Ricerche Sui Coloranti Cationic Per Fibra Acrylica," Chim. Ind. (Milan) vol. 56(No. 9), pp. 600-603 (1974).

Savarino et al., "Disperse and Cationic Dyes from Aminophenyl-X-Azolo-Pyridines," Dyes Pigm., vol. 11(No. 3), pp. 163-172 (1989).

Viscardi et al., "Disperse and Cationic Azo Dyes from Heterocyclic Intermediates," Dyes Pigm., vol. 19(No. 1) pp. 69-79 (1992).

Neidlin et al., "Synthese von substituierten Pyridiniumsalzen," Ger. Monatsh. Chem., vol. 106(No. 3), 643-648 (1975).

Tien et al., "Syntheses of New Azo Dyestuff Containing a Sydnone Ring," Journal of the Chinese Chemical Society (Taipei), vol. 45(No. 1), pp. 209-211 (1998).

Khim Tekhnol., vol. 22(No. 5) pp. 548-553 (1979).

Holla et al., "Studies on Nitrofuran Heterocycles, Part I," Rev. Roum. Chim., vol. 33(No. 4), pp. 277-282 (1998).

Alberti et al., "Thermodynamic Features in Acrylic Fiber Dyeing With Basic Dyes," Text. Res. J., vol. 54(No. 2), pp. 105-107 (1984).

Kuznetsova et al., "The determination of Thickness of a Histological Section by Interference Microscopy," Tsitologiya, vol. 10(No. 3), pp. 403-405 (1968).

Zh. Obshch. Khim., vol. 40(No. 1), pp. 195-202 (1970).

The Journal of General Chemistry of the USSR (translated from Russian), vol. 40(1), pp. 178-183. (English translation of Zh. Obshch. Khim., vol. 40(No. 1), pp. 195-202) (1970).

Whittemore et al., "Subtype-Selective N-Methyl-D-aspartate Receptor Antagonists: Benzimidazalone and Hydantoin as Phenol Replacements," Journal of Medicinal Chemistry, vol. 43(No. 9), pp. 1892-1897 (2000).

K. Venkateraman, *The Chemistry of Synthetic Dye*, vol. 1to 7 Academic Press (1952).

"Dyes and Dye Intermediate," *Kirk Othmer Encyclopedia of Chemical Technology*, 7$^{th}$ ed., Wiley and Sons (1993).

MRL Bull. Res. Dev. vol. 6, No. 2, pp. 21-27 (1992).

Lihua Jianyan, Huaxue Fence, vol. 29, No. 4, pp. 233-234 (1993).

English Language Derwent Abstract to DE 33 35 956.

English Language Derwent Abstract to DE 41 37 005.

English Language Derwent Abstract to DE 42 20 388.

* cited by examiner

LIGHTENING DYE COMPOSITION COMPRISING AT LEAST ONE CATIONIC DIRECT DYE CONTAINING MIXED CHROMOPHORES

This application claims benefit of U.S. Provisional Application No. 60/499,336, filed Sep. 3, 2003, the contents of which are incorporated herein by reference. This application also claims benefit of priority under 35 U.S.C. § 119 to French Patent Application No. 03 07186, filed Jun. 16, 2003, the contents of which are also incorporated by reference.

The invention relates to a dye composition comprising a cationic direct dye comprising different chromophores, in particular a composition for the lightening dyeing of keratin fibers. The invention also relates to the dyeing process using this composition, and to the use of this composition for lightening keratin fibers.

It is known practice to dye keratin fibers, and in particular human hair, with dye compositions containing oxidation dye precursors, which are generally known as oxidation bases, such as ortho- or para-phenylenediamines, ortho- or para-aminophenols and heterocyclic compounds. These oxidation bases are colorless or weakly colored compounds, which, when combined with oxidizing products, may give rise to colored compounds by a process of oxidative condensation.

It is also known that the shades obtained with these oxidation bases may be varied by combining them with couplers or coloration modifiers, the latter being chosen especially from aromatic meta-diamines, meta-aminophenols, meta-diphenols and certain heterocyclic compounds such as indole compounds.

The variety of molecules used as oxidation bases and couplers allows a wide range of colors to be obtained.

This oxidation dyeing process consists in applying to keratin fibers bases or a mixture of bases and of couplers with aqueous hydrogen peroxide solution as oxidizing agent, leaving the mixture to act on the fibers, and then rinsing the fibers. The colorations resulting therefrom are permanent, strong and resistant to external agents, especially to light, bad weather, washing, perspiration and rubbing. This process, which is generally performed at basic pH, makes it possible to obtain dyeing and simultaneous lightening of the fiber, which is reflected in practice by the possibility of obtaining a final coloration that is lighter than the original color. In addition, lightening of the fiber has the advantageous effect of creating a unified color in the case of gray hair, and of bringing out the color, i.e. of making it more possible, in the case of naturally pigmented hair.

It is also known practice to dye keratin fibers by direct dyeing. This process conventionally used in direct dyeing consists in applying to the keratin fibers direct dyes, which are colored and coloring molecules that have affinity for the fibers, leaving the dyes to act on the fibers, and then rinsing the fibers.

It is known practice, for example, to use direct dyes of the nitrobenzene type, anthraquinone dyes, nitropyridines, or dyes of the azo, xanthene, acridine, azine, or triarylmethane type.

These direct dyes may consist of one or more chromophores, which may be identical or different. Dyes consisting of several chromophores are described, for example, in documents FR 1 540 423, EP 1 133 975, EP 1 133 976, U.S. Pat. No. 5,708,151 and WO 02/078596.

The colorations resulting from the use of direct dyes are temporary or semi-permanent colorations, since the nature of the interactions that bind the direct dyes to the keratin fiber, and their desorption from the surface and/or the core of the fiber, are responsible for their poor dyeing power and their poor wash-fastness and perspiration-fastness.

Certain direct dyes may be combined with oxidizing agents, thus making it possible to obtain lightening of the fiber at the time of dyeing. For example, patent application EP 810 851 describes dye compositions containing direct dyes comprising at least one quaternized nitrogen atom of the azo or azomethine type, which may be mixed extemporaneously at basic pH with an oxidizing composition.

However, the colorations obtained are not always satisfactory as regards the fastness of the color. They disappear on shampooing, leaving the lightened keratin fiber to show through. Furthermore, when the dye composition contains a mixture of direct dyes, changing of the color over time takes place, this changing resulting from the difference in affinity of each of the dyes for the keratin fiber and from their resistance to external agents such as shampoo.

The aim of the present invention is to provide direct dyes that can be used in lightening dyeing but do not have the drawbacks of the existing direct dyes. In particular, one of the aims of the present invention is to provide direct dyes that are sufficiently stable in the presence of oxidizing and/or alkaline agents to be able simultaneously to obtain lightening and dyeing of the fiber. Another aim of the invention is to provide direct dyes that allow varied shades to be obtained without the problem of the color changing over time and that allow keratin fibers to be dyed as strongly as with oxidation dyes, which are as stable as said oxidation dyes to light, resistant to bad weather, washing and perspiration, and long-lasting.

This aim is achieved with the present invention, one aim of which is a lightening dye composition comprising, in a suitable dyeing medium, an oxidizing agent, an alkaline agent in an amount such that the pH of the composition is greater than 7, and a cationic mixed dye comprising several chromophores linked together via a linker, at least two of the chromophores being different, the chromophores exhibiting at least one absorption maximum between 400 and 800 nm.

A subject of the invention is also a dyeing process using this composition.

Another subject of the invention is the use of the composition of the present invention for dyeing keratin fibers, in particular human keratin fibers such as the hair, in particular to obtain good shampoo resistance.

Specifically, the composition of the present invention makes it possible to obtain a lightening of keratin fibers and a coloration which is fast with respect to various external agents, in particular shampoo. The composition furthermore makes it possible to avoid the problems of changing of the color over time.

The cationic mixed direct dyes that are useful in the present invention are in particular stable in a lightening composition containing an alkaline agent such as aqueous ammonia and/or an oxidizing agent such as hydrogen peroxide. In particular, the coloration of the locks of hair is not substantially modified when the mixed dye is used in a non-lightening composition, i.e. a composition containing no alkaline agent or any lightening agent, and when the mixed dye is used with a composition containing either an alkaline agent, for example aqueous ammonia, or an oxidizing agent, for example aqueous hydrogen peroxide solution, or simultaneously an alkaline agent and an oxidizing agent.

In the context of the invention, the term "cationic mixed dye" means a dye whose cationic charge can form an integral part of the chromophore and/or of the linker, or alternatively a dye whose cationic charge is present via a substituent on the chromophore and/or on the linker.

According to the present invention, the term "chromophore" means a radical derived from a dye, i.e. a radical of a molecule that has at least one absorption maximum in the visible region between 400 and 800 nm, this absorbance requiring no prior oxidation or any combination with other chemical species.

For the purposes of the present invention, the chromophores are said to be different when they differ in their chemical structure. Such chromophores may be chromophores derived from different families or from the same family, on condition that they have different chemical structures. For example, the chromophores may be chosen from the family of azo dyes, but differ in the chemical structure of the radicals of which they are composed.

According to one particular embodiment, the mixed dye comprises at least one cationic chromophore and preferably at least two cationic chromophores, the linker possibly being cationic or non-cationic.

As chromophores that are useful in the present invention, mention may be made of radicals derived from the following dyes: acridines, acridones, anthranthrones, anthrapyrimidines, anthraquinones, azines, azos, azomethines, benzanthrones, benzimidazoles, benzimidazolones, benzindoles, benzoxazoles, benzopyrans, benzothiazoles, benzoquinones, bis-azines, bis-isoindolines, carboxanilides, coumarins, cyanins (azacarbocyanin, diazacarbocyanin, diazahemicyanin, hemicyanin and tetraazacarbocyanin), diazines, diketopyrrolopyrroles, dioxazines, diphenylamines, diphenylmethanes, dithiazines, flavonoids such as flavanthrones and flavones, fluorindines, formazans, hydrazones, in particular arylhydrazones, hydroxy ketones, indamines, indanthrones, indigoids and pseudo-indigoids, indophenols, indoanilines, isoindolines, isoindolines, isoindolinones, isoviolanthrones, lactones, methines, naphthalimides, naphthanilides, naphtholactams, naphthoquinones, nitro dyes, especially nitro (hetero)aromatic dyes, oxadiazoles, oxazines, perilones, perinones, perylenes, phenazines, phenothiazines, phthalocyanin, polyenes/carotenoids, porphyrins, pyranthrones, pyrazolanthrones, pyrazolones, pyrimidinoanthrones, pyronines, quinacridones, quinolines, quinophthalones, squaranes, stilbenes, tetrazoliums, thiazines, thioindigo, thiopyronines, triarylmethanes, xanthenes.

As chromophores that are useful in the present invention, mention may be made even more particularly of radicals derived from the following dyes: acridines, acridones, anthranthrones, anthraquinones, azines, azos, azomethines, benzanthrones, benzoquinones, bis-azines, cyanins (azacarbocyanin, diazacarbocyanin, diazahemicyanin, hemicyanin and tetraazacarbocyanin), diazines, diketopyrrolopyrroles, dioxazines, diphenylmethanes, dithiazines, flavonoids such as flavanthrones and flavones, formazans, hydrazones, in particular arylhydrazones, indamines, indanthrones, indigoids and pseudo-indigoids, indophenols, indoanilines, isoviolanthrones, methines, naphthalimides, naphtholactams, naphthoquinones, nitro dyes, especially nitro(hetero)aromatic dyes, phenazines, phenothiazines, phthalocyanin, polyenes/carotenoids, porphyrins, pyrazolone, quinacridones, quinophthalones, tetrazoliums, thiazines, thioindigo, thiopyronines, triarylmethanes, xanthenes.

Among the nitro chromophores that may be used according to the invention, mention may be made in a non-limiting manner of the radicals derived from the following compounds:

1,4-diamino-2-nitrobenzene
1-amino-2-nitro-4-(β-hydroxyethylamino)benzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis-(β-hydroxyethylamino)benzene
1-β-hydroxyethylamino-2-nitro-4-aminobenzene
1-β-hydroxyethylamino-2-nitro-4-(ethyl)(β-hydroxy-ethyl) aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-[tris(hydroxymethyl)methylamino]-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene
1-hydroxy-4-β-hydroxyethylamino-3-nitrobenzene.

Among the azo chromophores that may be used according to the invention, mention may be made of the radicals derived from the cationic azo dyes described in patent applications WO 95/15144, WO-95/01772 and EP-714 954.

Mention may also be made, among the radicals derived from the following azo dyes, described in the Color Index International 3rd edition, of:

Disperse Red 17
Acid Yellow 9
Acid Black 1
Basic Red 22
Basic Red 76
Basic Yellow 57
Basic Brown 16
Acid Yellow 36
Acid Orange 7
Acid Red 33
Acid Red 35
Basic Brown 17
Acid Yellow 23
Acid Orange 24
Disperse Black 9.

Mention may also be made of 1-(4'-aminodiphenylazo)-2-methyl-4-[bis(β-hydroxyethyl)amino]benzene and 4-hydroxy-3-(2-methoxy-phenylazo)-1-naphthalenesulfonic acid.

Among the quinone chromophores that may be mentioned are the radicals derived from the following dyes:

Disperse Red 15
Solvent Violet 13
Acid Violet 43
Disperse Violet 1
Disperse Violet 4
Disperse Blue 1
Disperse Violet 8
Disperse Blue 3
Disperse Red 11
Acid Blue 62
Disperse Blue 7
Basic Blue 22
Disperse Violet 15
Basic Blue 99 and also the following compounds:
1-N-methylmorpholiniumpropylamino-4-hydroxy-anthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Among the azine chromophores that may be mentioned are the radicals derived from the following compounds:
Basic Blue 17
Basic Red 2.

Among the indoamine chromophores that may be used according to the invention, mention may be made of the radicals derived from the following compounds:
2-β-hydroxyethylamino-5-[bis(β-4'-hydroxyethyl)-amino]anilino-1,4-benzoquinone;
2-β-hydroxyethylamino-5-(2'-methoxy-4'-amino)anilino-1,4-benzoquinone;
3-N(2'-chloro-4'-hydroxy)phenylacetylamino-6-methoxy-1,4-benzoquinoneimine;
3-N(3'-chloro-4'-methylamino)phenylureido-6-methyl-1,4-benzoquinoneimine;
3-[4'-N-(ethylcarbamylmethyl)amino]phenylureido-6-methyl-1,4-benzoquinoneimine.

Mention may also be made of the chromophores described in documents U.S. Pat. No. 5,888,252, EP 1 133 975, WO 03/029359, EP 860 636, WO 95/01772, WO 95/15144 and EP 714 954. Mention may also be made of those mentioned in the encyclopedia "The chemistry of synthetic dye" by K. Venkataraman, 1952, Academic Press, vol. 1 to 7, in encyclopedia "Kirk-Othmer" "Chemical Technology", in the chapter "Dyes and Dye Intermediate", 1993, Wiley & Sons, and in various chapters of the encyclopedia "Ullmann's Encyclopedia of Industrial Chemistry" 7th edition, Wiley & Sons.

Preferably, the chromophores are chosen from azo, xanthene, hydrazone and especially arylhydrazone, phenothiazine, acridine, cyanin, for instance tetraazacarbocyanin, anthraquinone, methine, azomethine, diketopyrrolopyrrole, indigoid and nitro, especially nitro(hetero)aromatic, chromophores.

According to one even more particular embodiment, the chromophores are chosen from azo, hydrazone, especially arylhydrazone, cyanin, for instance tetraazacarbocyanin, anthraquinone, methine, azomethine and nitro, especially nitro(hetero)aromatic, chromophores.

The mixed cationic dye preferably comprises two to four different chromophores, and preferably two or three different chromophores.

According to a particular embodiment, the mixed dye is at least dicationic, the cationic fillers being borne by the chromophores and/or by the linker. According to a variant of this embodiment, at least two of the chromophores are cationic chromophores, the linker possibly being cationic.

Preferably, the mixed dye of the invention corresponds to the formula

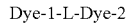

Dye-1-L-Dye-2 in which L is a cationic or non-cationic linker, and Dye 1 and Dye 2 are different cationic chromophores.

The cationic chromophore(s) is (are) generally chromophores comprising a quaternized nitrogen atom.

These cationic chromophores are, for example, chromophores comprising, directly or as substituent, an alkylammonium, imidazolium, pyridinium, quinolinium, acridinium, benzimidazolium, benzobistriazolium, benzopyrazolium (or indazolium), benzopyridazinium, benzoquinolium, benzothiazolium, benzotriazolium, benzoxazolium, bi-pyridinium, bis-tetrazolium, dihydrothiazolium, imidazopyridinium, indolium, isoquinolinium, naphthimidazolium, naphthoxazolium, naphthopyrazolium, oxadiazolium, oxazolium, oxazolopyridinium, phenazinium, phenoxazolium, pyrazinium, pyrazolium, pyrazoyltriazolium, pyridinoimidazolium, quinolium, tetrazolium, thiadiazolium, thiazolium, thiazolopyridinium, thiazoylimidazolium, thiopyrylium, triazolium or xanthylium radical.

Preferably, these chromophores comprise, directly or as substituent, an alkylammonium, imidazolium, pyridinium, acridinium, benzimidazolium, benzopyrazolium (or indazolium), benzopyridazinium, bi-pyridinium, bis-tetrazolium, imidazopyridinium, indolium, naphthimidazolium, naphthopyrazolium, phenazinium, pyrazinium, pyrazolium, pyridinoimidazolium, tetrazolium or xanthylium radical.

Examples of cationic chromophores that are useful in the present invention have been mentioned previously. Other examples are given in patent applications WO 95/01772, WO 95/15144, EP 714 954, EP 318 294 and WO 03/029359.

According to one variant, the mixed dye comprises cationic azo chromophores. Such chromophores are described, for example, in EP 0 850 636, FR 2 788 433, EP 920 856, WO 99/48465, FR 2 757 385, EP-850 637, EP 918 053, WO 97/44004, FR 2 570 946, FR 2 285 851, DE 2 538 363, FR 2 189 006, FR 1 560 664, FR 1 540 423, FR 1 567 219, FR 1 516 943, FR 1 221 122, DE 4 220 388, DE 4 137 005, WO 01/66646, U.S. Pat. No. 5,708,151, WO 95/01772, WO 95/15144, GB 1 195 386, U.S. Pat. No. 3,524,842, U.S. Pat. No. 5,879,413, EP 1 062 940, EP 1 133 976, GB 738 585, DE 2 527 638, FR 2 275 462, GB 1974-27645, Acta Histochem. (1978), 61(1), 48–52, Tsitologiya (1968), 10(3), 403–5, Zh. Obshch. Khim. (1970), 40(1), 195–202, Ann. Chim. (Rome) (1975), 65(5–6), 305–14, Journal of the Chinese Chemical Society (Taipei) (1998), 45(1), 209–211, Rev. Roum. Chim. (1988), 33(4), 377–83, Text. Res. J. (1984), 54(2), 105–7, Chim. Ind. (Milan) (1974), 56(9), 600–3, Khim. Tekhnol. (1979), 22(5), 548–53, Ger. Monatsh. Chem. (1975), 106(3), 643–8, MRL Bull. Res. Dev. (1992), 6(2), 21–7, Lihua Jianyan, Huaxue Fence (1993), 29(4), 233–4, Ann. Chim. (Rome) (1975), 65(5–6), 305–14, Dyes Pigm. (1992), 19(1), 69–79, Dyes Pigm. (1989), 11(3), 163–72.

In the context of the present invention, the term "linker" means an atom or a group of atoms separating the chromophores from the mixed dye. The atoms of the linker must be such that the position on the scale of wavelengths of the absorption maxima(s) of the chromophores constituting the mixed dye should not be modified by more than 30 nanometers relative to the absorption maxima of each of the chromophores taken separately, i.e. not linked together via the linker, more particularly not more than 15 nm and preferably not more than 10 nm. The linker may be cationic or non-cationic. Preferably, the linker is non-cationic.

According to one variant, the linker is an atom or a group of atoms that isolates each of the chromophores so as to stop electronic delocalization of each of the chromophores.

The linker is, for example, a $C_1$–$C_{20}$, preferably $C_1$–$C_{14}$ and even more particularly $C_1$–$C_6$, linear, branched or cyclic, optionally substituted hydrocarbon-based chain, one or more of the carbon atoms of the chain possibly being replaced with at least one hetero atom such as sulfur, nitrogen or oxygen, and/or with at least one group comprising a hetero atom, such as a carbonyl group, the hydrocarbon-based chain possibly being unsaturated or containing at least one optionally substituted alkylene radical; an optionally substituted arylene radical; an optionally substituted divalent terephthalamide radical; an optionally substituted divalent heterocyclic radical, for instance a divalent triazine radical, or an —NH—CO— radical.

The hydrocarbon-based chain, but also the alkyl(en)e radicals, may be substituted, for example, with at least one hydroxyl radical, an alkoxy radical, especially of C1–C6, a C1–C6 (poly)hydroxyalkoxy group, an amino group, an alkylamino group comprising one or more identical or different C1–C6 alkyl radicals optionally bearing at least one hydroxyl group, at least one halogen, etc.

Examples of linkers that may be mentioned include alkylene radicals ($C_nH_{2n}$) more especially containing 1 to 14 carbon atoms and preferably 1 to 6 carbon atoms, for example methylene, ethylene, propylene, etc., optionally substituted as indicated above, optionally interrupted with at least one hetero atom such as sulfur, nitrogen or oxygen, and/or a group comprising a hetero atom such as a carbonyl group; optionally substituted (hetero)arylene radicals, for example phenylene or naphthylene, phenanthrylene, triazinyl, pyrimidinyl, pyridyl, pyridazinyl, or quinoxalinyl, which are optionally substituted; Alkyl-aryl-Alkyl radicals or Alkyl-heteroaryl-Alkyl radicals, the alkyl portions of the radicals more particularly comprising from 1 to 6 carbon atoms.

The (hetero)arylene radicals mentioned above may be substituted with one or more of the following radicals: C1–C6 alkyl; C1–C6 alkoxy; C2–C6 (poly)hydroxyalkoxy; amino; amino substituted with one or more identical or different C1–C6 alkyl radicals optionally bearing at least one hydroxyl group and/or substituted with a C6 aryl radical optionally substituted with one or more C1–C6 alkyl, C1–C6 alkoxy, C2–C6 (poly)hydroxyalkoxy or amino groups, or amino groups substituted with one or more identical or different C1–C6 alkyl radicals optionally bearing at least one hydroxyl group; trifluoromethyl; cyano; alkylamido, especially of C1–C6; RCOO— with R representing a C1–C6 alkyl radical.

More particular examples that may be mentioned include:

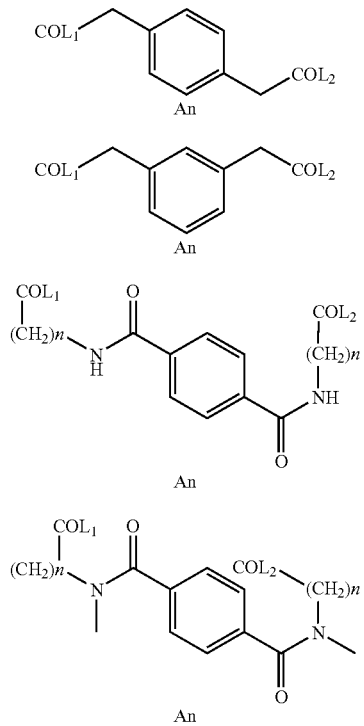

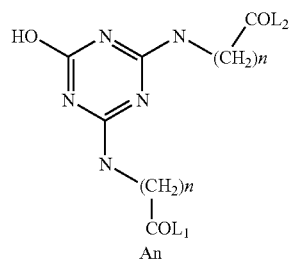

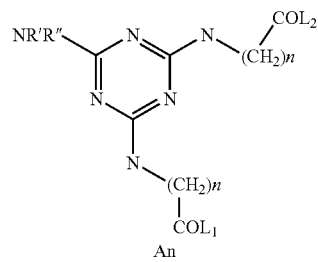

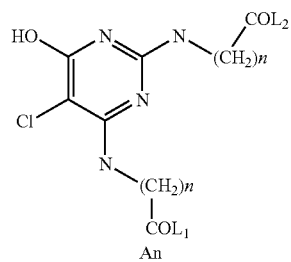

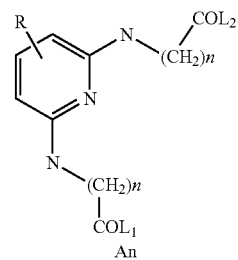

in which R may be H, $CF_3$, $CO_2Me$, $CO_2Et$, CN or $CONH_2$, R' represents a hydrogen atom, a $C_1$–$C_8$ alkyl radical optionally substituted with one or more hydroxyl, $C_1$–$C_2$ alkoxy, $C_2$–$C_4$ (poly)hydroxyalkoxy, amino, $C_1$–$C_2$ (di)alkylamine or optionally substituted aryl radicals, and R" represents a hydrogen atom, a $C_1$–$C_4$ alkyl radical optionally substituted with one or more hydroxyl, $C_1$–$C_2$ alkoxy, $C_2$–$C_4$ (poly) hydroxyalkoxy, amino, $C_1$–$C_2$ (di)alkylamino or optionally substituted aryl radicals, n is greater than 0, more particularly between 1 and 10 and preferably between 1 and 5; the electrical neutrality of the compounds being ensured by means of one or more cosmetically acceptable anions An.

Linkers that may be mentioned include the triazines described in WO 03/029359, the alkylenes mentioned in U.S. Pat. No. 5,708,151 and the Alkyl-aryl-Alkyls mentioned in U.S. Pat. No. 5,708,151.

It should be noted that any alkylene group in the main chain linking Dye 1/Dye 2, for the purposes of the present invention, is considered as being a linker.

An is an organic or mineral anion chosen, for example, from halides such as chlorides, bromides, fluorides or iodides; hydroxides, sulfates; hydrogen sulfates; $(C_1-C_6)$ alkyl sulfates, for instance methyl sulfate or ethyl sulfate; phosphates; carbonates; hydrogen carbonates; perchlorates; acetates; tartrates; citrates; oxalates; $(C_1-C_6)$alkylsulfonates such as methanesulfonate; arylsulfonates optionally substituted with a $C_1-C_4$ alkyl radical, for instance a 4-tolylsulfonate.

According to a particular embodiment, the mixed dyes may be represented by the formula:

C1–C6, optionally substituted with one or more hydroxyl, $C_1-C_2$ alkoxy, $C_2-C_4$ (poly)hydroxyalkoxy, amino, $C_1-C_2$ (di)alkylamino or optionally substituted aryl radicals and R2 and R2' are independently chosen from a $C_1-C_6$ alkyl radical, optionally substituted with one or more hydroxyl, $C_1-C_2$ alkoxy, $C_2-C_4$ (poly)hydroxyalkoxy, amino or $C_1-C_2$ (di)alkylamino radicals; an optionally substituted phenyl radical; An represents one or more identical or different, monovalent or multivalent anions, as defined previously.

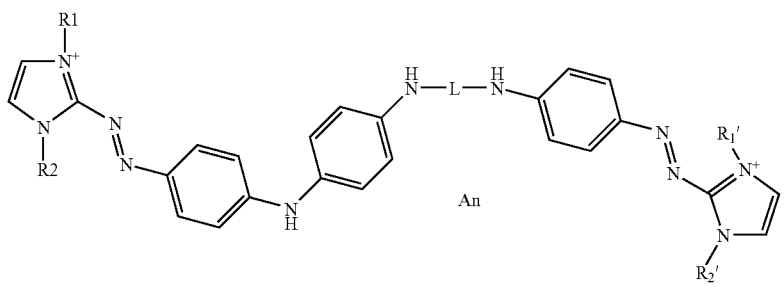

in which L is a linker as defined above, R1 and R1' are independently chosen from an alkyl radical, preferably of Examples of cationic direct dyes corresponding to this formula that may be mentioned include:

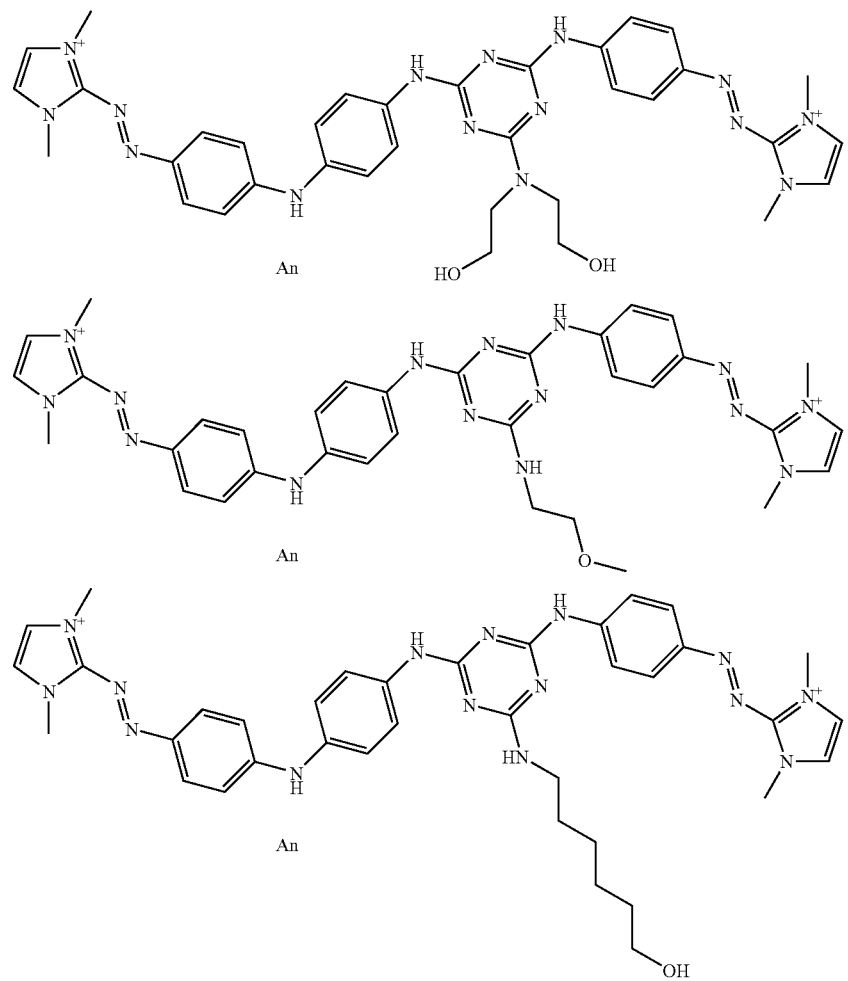

-continued

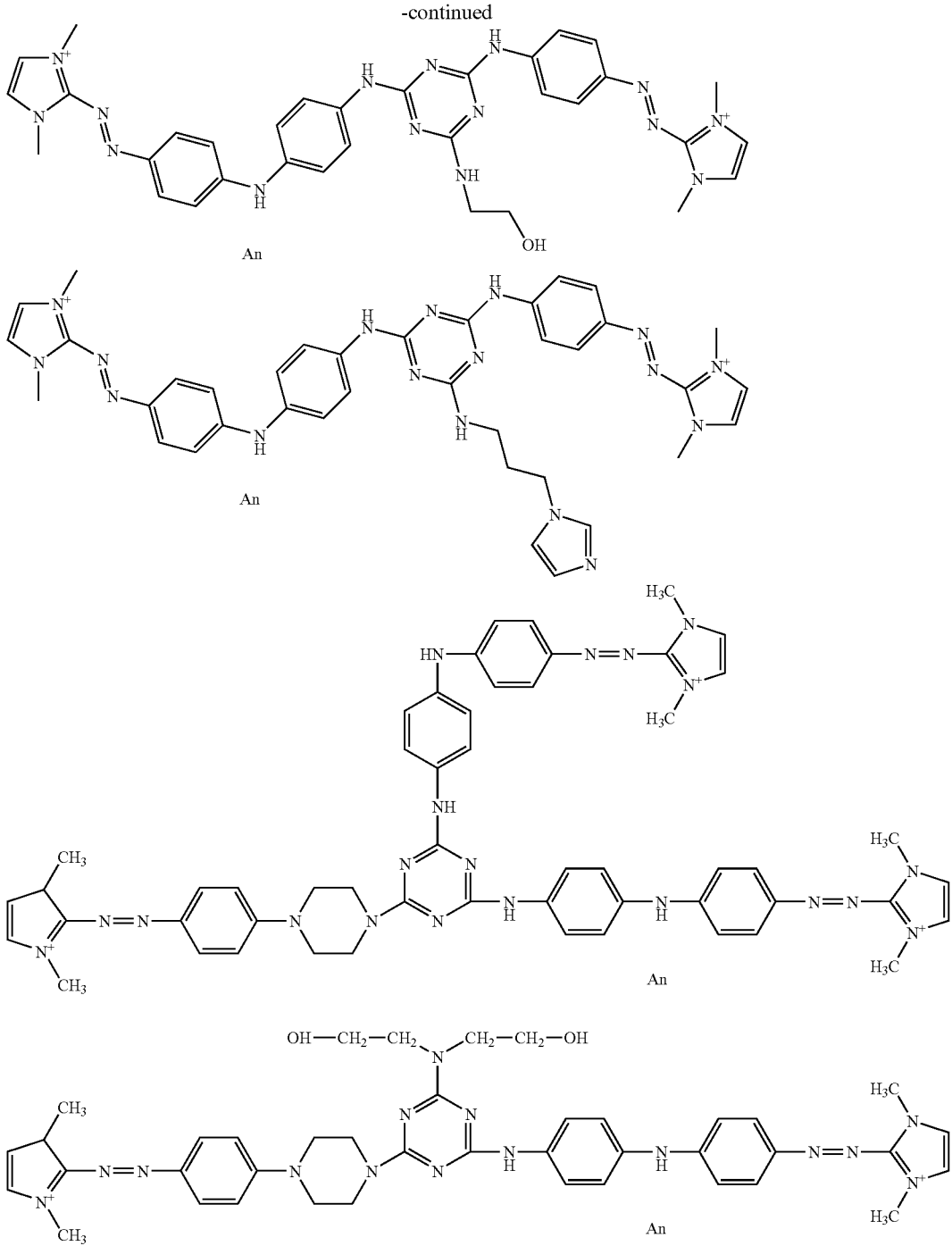

The composition of the present invention generally contains an amount of mixed dye of between 0.001% and 20% relative to the total weight of the composition. Preferably, this amount is between 0.005% and 10% and even more preferably between 0.01% and 5% relative to the total weight of the composition.

The dyes of the invention may be prepared according to chemical reactions that are known per se, starting with functionalized chromophores capable of reacting with the chosen linker. For example, when the linker is a triazine group, then the chromophore should comprise a reactive amino, OH or SH group and the synthesis may be performed according to the schemes below.

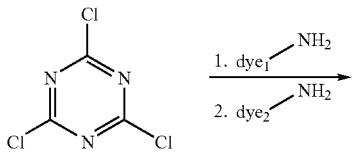

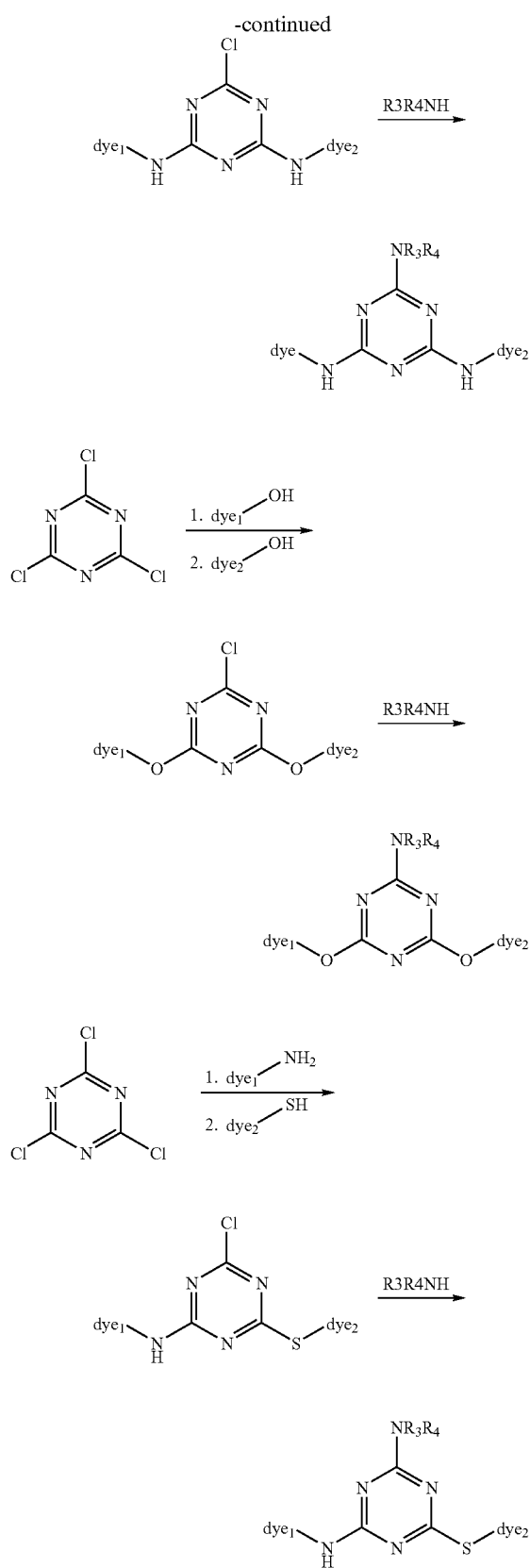

According to a first step, a first chromophore is mixed with the compound forming or capable of forming the linker, for example cyanuric chloride. When this reaction is complete, a second chromophore is added to the reaction medium. This sequence may be repeated as many times as there are reactive groups on the compound capable of forming the linker.

For the preparation of a mixed dye Dye 1-L-Dye 2, the molar ratio of the linker relative to dye 1 is generally between 10:1 and 0.5:1 and preferably equal to 1:1. This ratio may be modified when more than one linker or several chromophores are used.

The reaction temperature is generally between −10° C. and +130° C. and preferably between −5° C. and 100° C.

The reaction time depends on the reactivity of the species present and on the reaction temperature. In general, the reaction time is between 10 minutes and 8 hours and preferably between 30 minutes and 4 hours.

The pH of the reaction is generally between 3 and 10 and preferably between 4 and 8.

The reaction may be performed in water and/or in organic solvents, alone or as mixtures. Several publications describe the reaction for the chemical combination between two identical chromophores. Examples that may be mentioned include the documents ISBN 0901956759, WO 02/78596, DE 198 45 640, WO 03/029359 and U.S. Pat. No. 5,708,151.

In addition, the reactions or the reactions of a linker with two different compounds, which may or may not be dyes, have been described in the literature, for example in WO 03/029359, DE 3 335 956, WO 03/30909, WO 03/18021, Journal of Medicinal Chemistry 43(9), 2000, 1892–97; Chemiker Zeitung 117(7–8), 1987, 241–5.

The composition of the invention contains an alkaline agent, which may be any alkaline agent generally used in cosmetics. Among these alkaline agents that may be mentioned, for example, are aqueous ammonia, alkaline carbonates, alkanolamines such as mono-, di- and triethanolamine and derivatives thereof, sodium hydroxide, potassium hydroxide and the compounds of formula (II) below:

(II)

in which W is a propylene residue that is unsubstituted or substituted with a hydroxyl group or a $C_1$–$C_4$ alkyl radical; $R_a$, $R_b$, $R_c$ and $R_d$, which may be identical or different, represent a hydrogen atom, a $C_1$–$C_4$ alkyl radical or a $C_1$–$C_4$ hydroxyalkyl radical.

The pH of the dye composition of the invention is preferably between 8 and 11.

The composition of the invention contains an oxidizing agent. The oxidizing agents conventionally used for the oxidation dyeing of keratin fibers are, for example, hydrogen peroxide, urea peroxide, alkali metal bromates, persalts such as perborates and persulfates, peracids and oxidase enzymes, among which mention may be made of peroxidases, 2-electron oxidoreductases such as uricases, and 4-electron oxygenases, for instance laccases. Hydrogen peroxide is particularly preferred.

The dye composition in accordance with the invention may contain one or more direct dyes conventionally used in the field of dyeing keratin fibers. In this respect, mention may be made especially of nitrobenzene dyes, azo direct dyes and methine direct dyes. These direct dyes may be of nonionic, anionic or cationic nature. Preferably, these additional direct dyes are of cationic nature.

The dye composition of the invention may also contain one or more oxidation bases and/or one or more couplers conventionally used for dyeing keratin fibers.

Among the oxidation bases that may be mentioned are para-phenylenediamines, bis(phenyl)-alkylenediamines, para-aminophenols, bis-para-aminophenols, ortho-aminophenols and heterocyclic bases, and the addition salts thereof.

Among these couplers that may especially be mentioned are meta-phenylenediamines, meta-amino-phenols, meta-diphenols, naphthalene-based couplers and heterocyclic couplers, and the addition salts thereof.

In the composition of the present inventions the coupler(s) is (are) each generally present in an amount of between 0.001% and 10% and preferably between 0.005% and 6% by weight approximately, relative to the total weight of the dye composition.

The oxidation base(s) present in the composition of the invention is (are) each generally present in an amount of between 0.001% and 10% and preferably between 0.005% and 6% by weight approximately, relative to the total weight of the dye composition.

In general, the addition salts of the oxidation bases and of the couplers that may be used in the context of the invention are especially chosen from the addition salts with an acid, such as the hydrochlorides, hydrobromides, sulfates, alkyl sulfates, for instance methyl or ethyl sulfates, citrates, succinates, tartrates, lactates, tosylates, benzenesulfonates, phosphates and acetates, and the addition salts with a base, such as sodium hydroxide, potassium hydroxide, ammonia, amines or alkanolamines.

The medium that is suitable for dyeing, also known as the dye support, is a cosmetic medium that generally consists of water or a mixture of water and at least one organic solvent to dissolve the compounds that would not be sufficiently soluble in water. As organic solvent, mention may be made, for example, of $C_1$–$C_4$ lower alkanols, such as ethanol and isopropanol; polyols and polyol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, and mixtures thereof.

The solvents are preferably present in proportions preferably of between 1% and 40% by weight approximately relative to the total weight of the dye composition, and even more preferably between 5% and 30% by weight approximately.

The dye composition in accordance with the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric associative polymeric thickeners, antioxidants, penetration agents, sequestering agents, fragrances, buffers, dispersing agents, packaging agents such as, for example, silicones, which may or may not be volatile or modified, film-forming agents, ceramides, preserving agents and opacifiers.

The above adjuvants are generally present in an amount for each of them of between 0.01% and 20% by weight relative to the weight of the composition.

Needless to say, a person skilled in the art will take care to select this or these optional additional compounds such that the advantageous properties intrinsically associated with the oxidation dye composition in accordance with the invention are not, or are not substantially, adversely affected by the addition(s) envisaged.

The dye composition according to the invention may be in various forms, such as in the form of liquids, creams or gels, or in any other form that is suitable for dyeing keratin fibers, and especially human hair.

The process of the present invention is a process in which the composition according to the present invention as defined above is applied to the fibers. The oxidizing agent may be added to the composition at the time of use, or it may be implemented starting with an oxidizing composition containing it, applied simultaneously or sequentially to the composition containing the mixed dye. In this case, the oxidizing agent is contained in a different composition from the one containing the mixed dye.

According to one particular embodiment, the composition according to the present invention containing the mixed dye is mixed, preferably at the time of use, with a composition containing, in a medium that is suitable for dyeing, at least one oxidizing agent, this oxidizing agent being present in an amount that is sufficient to obtain the desired lightening. The mixture obtained is then applied to the keratin fibers. After an action time of 3 to 50 minutes approximately, preferably 5 to 30 minutes approximately, the keratin fibers are rinsed, washed with shampoo, rinsed again and then dried.

The oxidizing composition may also contain various adjuvants conventionally used in compositions for dyeing the hair and as defined above.

The pH of the oxidizing composition containing the oxidizing agent is such that, after mixing with the dye composition, the pH of the resulting composition applied to the keratin fibers ranges preferably between 7 and 12 approximately and even more preferably between 8 and 11. It may be adjusted to the desired value by means of acidifying or basifying agents usually used in the dyeing of keratin fibers and as defined above.

The ready-to-use composition that is finally applied to the keratin fibers may be in various forms, such as in the form of liquids, creams or gels or any other form that is suitable for dyeing keratin fibers, and especially human hair.

Another subject of the invention is a multi-compartment dyeing device or "kit", in which a first compartment contains a lightening dye composition containing the mixed cationic dye as defined above and a second compartment contains an oxidizing agent. This device may be equipped with a means for applying the desired mixture to the hair, such as the devices described in patent FR-2 586 913 in the name of the Applicant.

The examples below illustrate the invention without, however, limiting its scope.

EXAMPLES

Examples of Synthesis

Step 1:

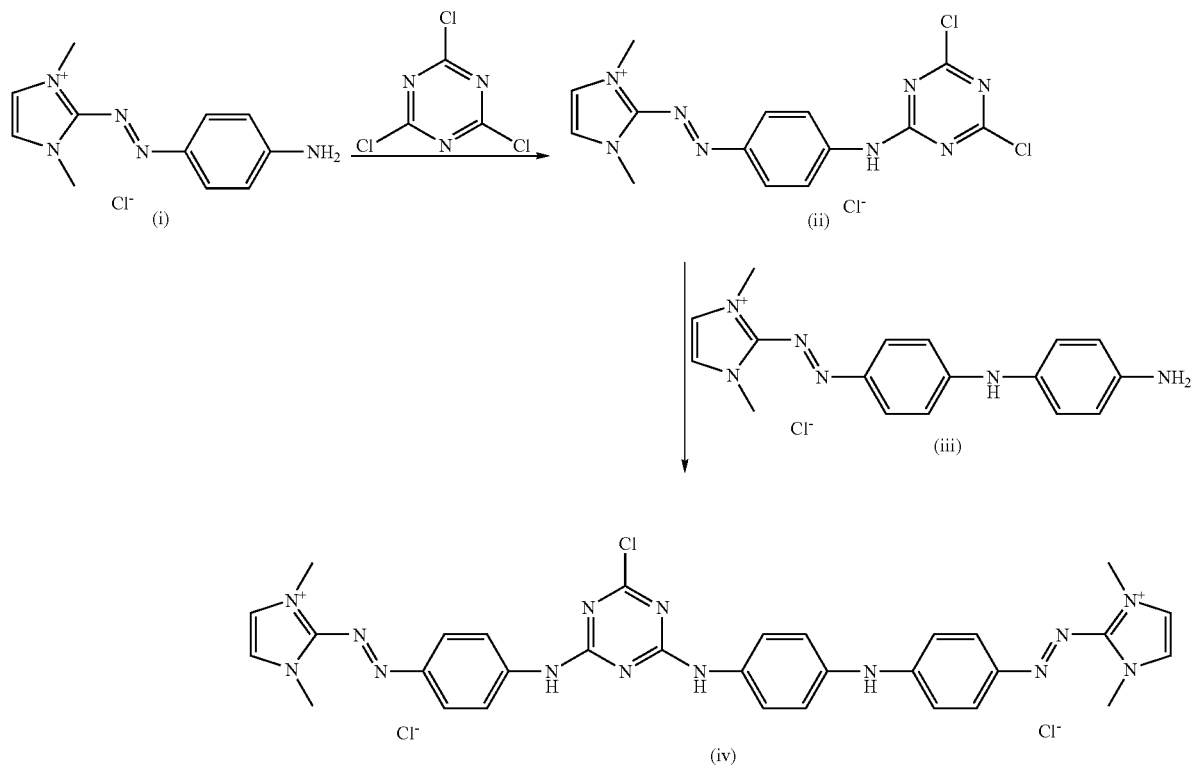

2.4 g of cyanuric chloride in 50 ml of acetone are added at room temperature and with stirring into a 500 ml three-necked flask. The reaction medium is transparent. A mixture consisting of water and ice in a respective proportion of 50 ml and 100 ml is added, and the reaction medium is placed at 0° C. in an ice bath.

After stirring for a few seconds, a whitish suspension is obtained. The pH value is 2.8. Using a dropping funnel, a solution containing 3.2 g of (i) dissolved in 100 ml of water is added, taking care to maintain the pH of the reaction medium at between 4 and 6 by means of saturated $K_2CO_3$ solution, and to keep the reaction medium at a temperature below 5° C.

After this addition, the pH is stabilized to 4.8 by uniform addition of saturated $K_2CO_3$ solution. The mixture is then allowed to return to room temperature. HPLC (relative purity: 94%) and a control mass (m/z: 363–365–367) indicate the virtually exclusive formation of the reaction product (ii).

A solution consisting of 3.42 g of (iii) predissolved in 50 ml of an $H_2O$/EtOH mixture (1/1) is then added to the above reaction medium, taking care to maintain the pH between 4 and 6. After addition, the pH is maintained at 4.9–5 for 15 minutes. The reaction medium is then heated at 44° C. for 2.5 hours. The reaction medium is allowed to return to room temperature and is then poured into a conical flask containing 1 liter of a solution consisting of isopropanol and acetone. A precipitate appears. This precipitate is filtered off, dried in a desiccator and then analyzed. 6.08 g (yield=86%) of a brown powder (product (iv)) are obtained in a purity equal to 98% (relative purity, HPLC).

Step 2:

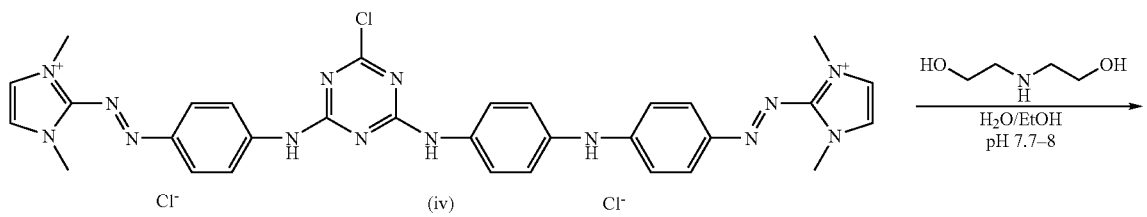

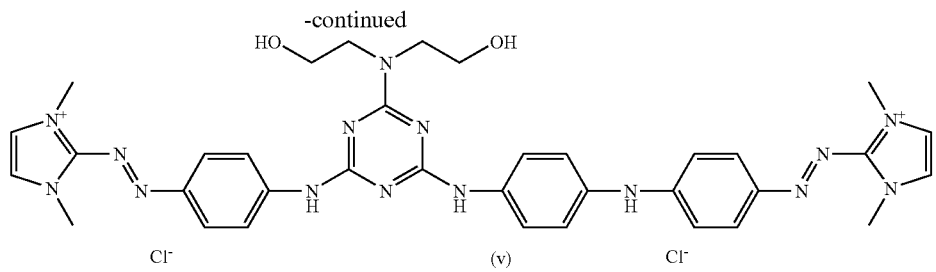
(v)

9 g of (iv) dissolved in 300 ml of water are placed in a three-necked flask on which is mounted a condenser, a pH probe and an addition funnel containing 1N sodium hydroxide solution. The reaction medium is then heated to 85° C. (oil bath temperature: 96° C.) and the pH is adjusted to between 7.7 and 8 using the sodium hydroxide solution. The amine (3 ml) diluted in 20 ml of water is then added very slowly, taking care to monitor the pH (pH<8). As soon as the addition is complete, the reaction medium is brought to 92° C. (oil bath temperature: 118° C.) and is stirred until the pH stabilizes at a value of between 7.7 and 8.

After reaction for one hour, the reaction medium is cooled and then poured into a conical flask containing 1 liter of acetone. The product precipitates out. It is then filtered off, dried in a desiccator and then analyzed. 7.1 g of a brown powder (compound v) are obtained (yield=82%, HPLC purity: 92%).

Mass (ESI+): m/z=352 NMR ($^1$H, 400 MHz, MeOD): 3.86–3.87 ppm (broad s, 4H), 4.05 ppm (s, 6H), 4.12 ppm (s, 6H), 4.88 ppm (broad s, 4H), 7.10–7.12 ppm (d, 2H), 7.28–7.26 ppm (d, 2H), 7.55 ppm (s, 2H), 7.69 ppm (s, 2H), 7.77–7.79 ppm (d, 2H), 7.97–7.95 ppm (d, 2H), 8.09–8.04 ppm (m, 4H).

The following compounds were synthesized by performing step 2 using the reagents indicated below.

| Structure of R | Reagent used | Mass (ESI +) m/z | HPLC purity (%) | Yield (%) |
|---|---|---|---|---|
| ⌇⌇NH* (propyl-NH*) | ⌇⌇NH$_2$ (propylamine) | 329 | 95 | 48 |
| ⌇O⌇NH* (methoxyethyl-NH*) | ⌇O⌇NH* (methoxyethyl-NH*) | 337 | 97 | 73 |
| HO⌇⌇⌇⌇N* (hydroxyhexyl-N*-CH3) | HO⌇⌇⌇⌇NH-CH3 | 358 | 97 | 61 |
| imidazole-propyl-*NH | imidazole-propyl-NH$_2$ | 362 | 97 | 82 |

-continued

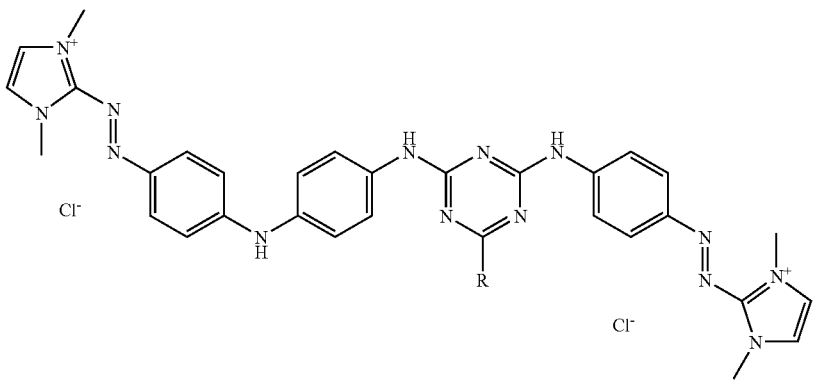

| Structure of R | Reagent used | Mass (ESI +) m/z | HPLC purity (%) | Yield (%) |
| --- | --- | --- | --- | --- |
| HO‑CH₂CH₂‑*NH | HO‑CH₂CH₂‑NH₂ | 330 | 98 | 94 |
| *N-piperazinyl-methyl | HN-piperazinyl-methyl | 349 | 98 | 71 |
| *N-morpholinyl | HN-morpholinyl | 342 | 95 | 56 |
| long alkyl-*NH | long alkyl-NH₂ | 371 | 74 | 66 |

Examples of Dyeing

The dye compositions described in table 1 were prepared from the dyes C1 to C5 (amount: $4.7 \times 10^{-4}$ mol) and from the following dye compositions:

Composition A

| | |
| --- | --- |
| (50/50 C8/C10) alkyl polyglucoside as a buffered aqueous 60% solution, sold under the name Oramix by the company SEPPIC | 10 g |
| Benzyl alcohol | 10 g |
| Polyethylene glycol 400 containing 8 ethylene oxide units | 12 g |
| Mixed dye C1 to C5 | $4.7 \times 10^{-4}$ mol |
| 20.5% aqueous ammonia | 13 g |
| Demineralized water | qs 100 g |

Composition B

| | |
| --- | --- |
| (50/50 C8/C10) alkyl polyglucoside as a buffered aqueous 60% solution, sold under the name Oramix by the company SEPPIC | 10 g |
| Benzyl alcohol | 10 g |
| Polyethylene glycol 400 containing 8 ethylene oxide units | 12 g |
| Mixed dye C1 to C5 | $4.7 \times 10^{-4}$ mol |
| Aminomethylpropanol | qs pH 10.5 |
| Demineralized water | qs 100 g |

| Dye | Chemical structure |
|---|---|
| C1 | 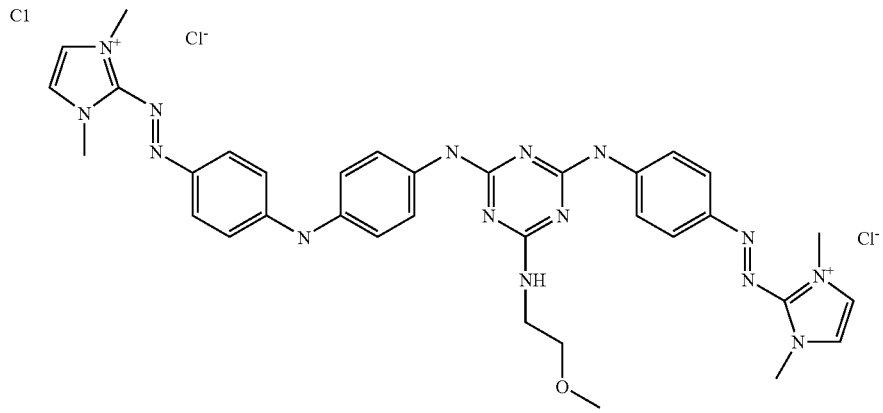 |
| C2 | 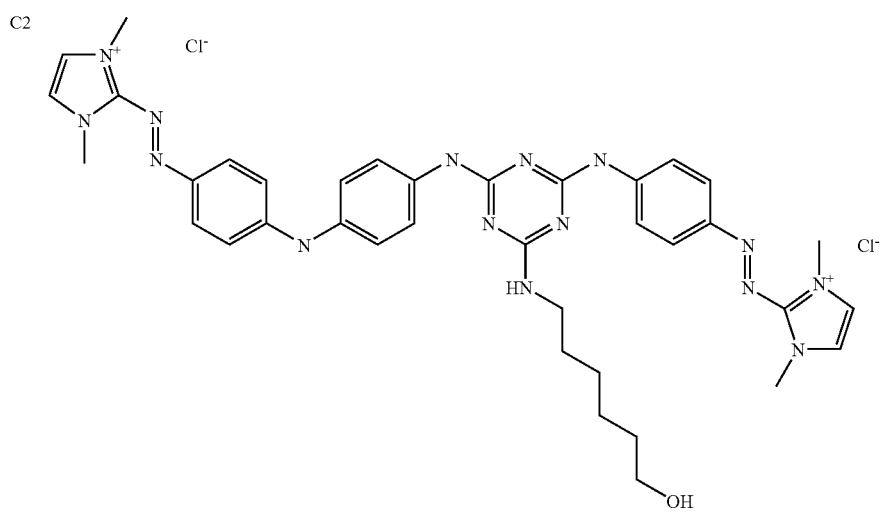 |
| C3 | 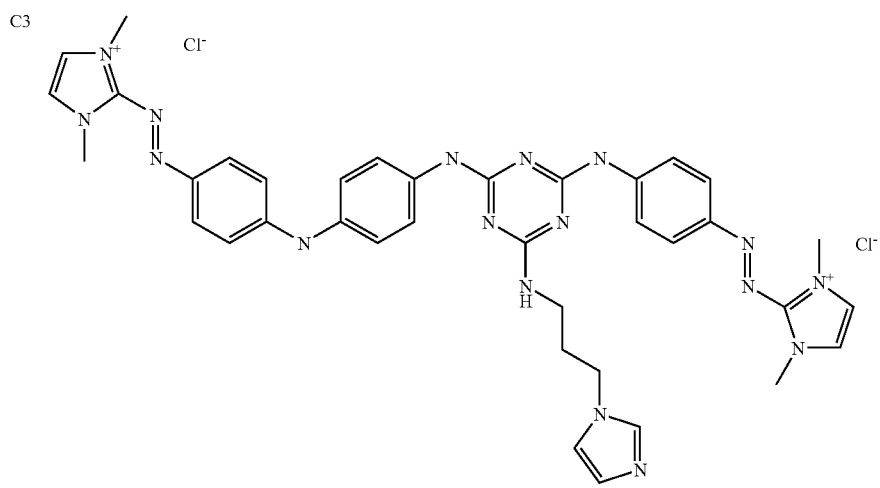 |

-continued

| Dye | Chemical structure |
|---|---|
| C4 | 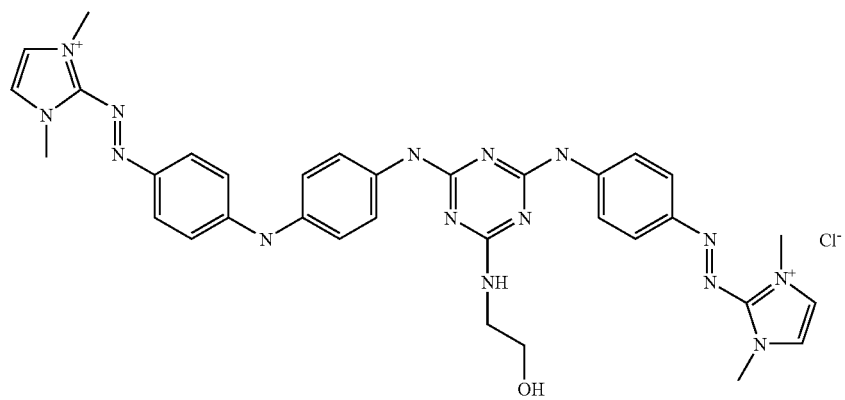 |
| C5 | 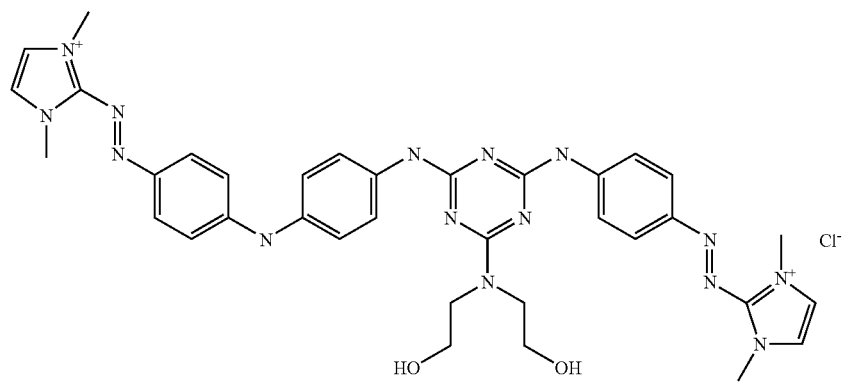 |

At the time of use, each of the above compositions is mixed either with 40 V (weight for weight, pH=3.5) aqueous hydrogen peroxide solution or with acidified water (pH=3.5).

The pH of the dye compositions after mixing is between 9.5 and 10.

The mixture is then applied to locks of natural gray (NG) or permanent-waved gray (PG) hair containing 90% white hairs. The leave-in time on the locks is 20 minutes at room temperature. The locks are then shampooed.

After drying, the color uptake is evaluated visually and by measuring the L*a*b* (CM 2002 colorimeter, illuminant D65-10° CSI).

The results are collated in table 1 below.

TABLE 1

| Type of hair | Composition | L* | a* | b* | "lightening/-nonlightening dye" comparison |
|---|---|---|---|---|---|
| NG | C1 + A + $H_2O_2$ | 36.7 | 3.0 | 2.5 | |
| | C1 + A + acidified water | 37.7 | 3.0 | 3.0 | |
| | C1 + B + $H_2O_2$ | 36.5 | 3.1 | 1.0 | |
| | C1 + B + acidified water | 37.2 | 3.4 | 1.4 | 1.3 |

TABLE 1-continued

| Type of hair | Composition | L* | a* | b* | "lightening/-nonlightening dye" comparison |
|---|---|---|---|---|---|
| PG | C1 + A + $H_2O_2$ | 34.5 | 2.0 | 2.5 | |
| | C1 + A + acidified water | 35.6 | 2.5 | 2.2 | |
| | C1 + B + $H_2O_2$ | 35.2 | 2.4 | 2.0 | |
| | C1 + B + acidified water | 35.5 | 2.7 | 1.4 | 1.6 |
| NG | C2 + A + $H_2O_2$ | 36.2 | 3.5 | 1.2 | |
| | C2 + A + acidified water | 36.4 | 3.3 | 2.5 | |
| | C2 + B + $H_2O_2$ | 36.3 | 4.0 | 0.2 | |
| | C2 + B + acidified water | 37.6 | 4.0 | 0.0 | 1.9 |
| PG | C2 + A + $H_2O_2$ | 33.9 | 3.0 | 0.7 | |
| | C2 + A + acidified water | 36.2 | 3.5 | 0.9 | |
| | C2 + B + $H_2O_2$ | 36.1 | 4.2 | −0.4 | |
| | C2 + B + acidified water | 36.6 | 3.8 | 0.6 | 2.8 |
| NG | C3 + A + $H_2O_2$ | 35.6 | 3.3 | 0.9 | |
| | C3 + A + acidified water | 36.5 | 3.1 | 1.5 | |
| | C1 + B + $H_2O_2$ | 36.9 | 4.1 | 0.0 | |
| | C3 + B + acidified water | 36.3 | 3.1 | 1.5 | 0.9 |

TABLE 1-continued

| Type of hair | Composition | L* | a* | b* | "lightening/-nonlightening dye" comparison |
|---|---|---|---|---|---|
| PG | C3 + A + H₂O₂ | 34.2 | 2.4 | 1.5 | |
| | C3 + A + acidified water | 35.1 | 2.5 | 1.3 | |
| | C3 + B + H₂O₂ | 33.5 | 2.4 | 1.1 | |
| | C3 + B + acidified water | 34.6 | 2.7 | 1.1 | 0.6 |
| NG | C4 + A + H₂O₂ | 36.0 | 3.7 | 1.0 | |
| | C4 + A + acidified water | 37.7 | 3.8 | 1.0 | |
| | C4 + B + H₂O₂ | 36.4 | 3.5 | 1.3 | |
| | C4 + B + acidified water | 37.4 | 4.0 | 0.9 | 1.4 |
| PG | C4 + A + H₂O₂ | 34.1 | 2.0 | 2.3 | |
| | C4 + A + acidified water | 34.7 | 2.5 | 1.5 | |
| | C4 + B + H₂O₂ | 34.8 | 2.9 | 1.5 | |
| | C4 + B + acidified water | 35.5 | 3.1 | 0.9 | 2.3 |
| NG | C5 + A + H₂O₂ | 36.2 | 3.2 | −0.2 | |
| | C5 + A + acidified water | 38.4 | 3.3 | 0.0 | |
| | C5 + B + H₂O₂ | 37.0 | 3.5 | 0.2 | |
| | C5 + B + acidified water | 36.7 | 3.2 | 0.5 | 0.6 |
| PG | C5 + A + H₂O₂ | 33.5 | 2.8 | 0.7 | |
| | C5 + A + acidified water | 35.4 | 2.9 | 0.2 | |
| | C5 + B + H₂O₂ | 34.4 | 3.0 | 0.9 | |
| | C5 + B + acidified water | 36.5 | 3.5 | −0.1 | 3.2 |

The comparison between the lightening and non-lightening conditions is calculated in the following manner:

$$\Delta E = \sqrt{(L_l^* - L_{nl}^*)^2 + (a_l^* - a_{nl}^*)^2 + (b_l^* - b_{nl}^*)^2}$$

in which $L_l^*$, $a_l^*$ and $b_l^*$ represent the colorimetric values under lightening conditions, and $L_{nl}^*$, $a_{nl}^*$ and $b_{nl}^*$ represent the colorimetric values under non-lightening conditions.

These results show that strong colorations that are insensitive to the composition of the dyeing medium are obtained. Specifically, similar colorations are obtained under lightening conditions (medium A+H₂O₂) and under non-lightening conditions (medium B+acidifed water).

Shampoo Fastness

The following dye compositions were prepared from the dyes D1 to D5 (4.7×10⁻⁴ mol) and the dye support A.

At the time of dyeing, the above compositions are mixed with 40V aqueous hydrogen peroxide solution (weight for weight, pH=3.5). The pH of the dye compositions after mixing is between 9.5 and 10.

The colored locks are then shampooed 6 times, with intermediate drying between two shampoo washes. The color after the 6 shampoo washes is compared with the initial color of the dyed lock, visually and by calorimetric measurement. The shampoo fastness is measured on dyed natural hair and on dyed permanent-waved hair according to the formula for ΔE below, using the L*a*b* values measured on each type of lock before $L_0^* a_0^* b_0^*$ and after the 12 shampoo washes $L_1^* a_1^* b_1^*$ $$\Delta E = \sqrt{(L_1^* - L_0^*)^2 + (a_1^* - a_0)^2 + (b_1^* - b_0^*)^2}$$

The calorimetric measurements are collated in table 2 below.

TABLE 2

| Type of hair | Composition | L* | a* | b* | Shampoo fastness |
|---|---|---|---|---|---|
| NG/before shampooing | C1 + A + H₂O₂ | 37.1 | 3.2 | 1.9 | 2.8 |
| NG/after shampooing | C1 + A + H₂O₂ | 34.4 | 2.4 | 2.2 | |
| PG/before shampooing | C1 + A + H₂O₂ | 34.9 | 1.8 | 3.1 | 2.4 |
| PG/after shampooing | C1 + A + H₂O₂ | 36.5 | 3.2 | 2.0 | |
| NG/before shampooing | C2 + A + H₂O₂ | 36.1 | 3.4 | 1.2 | 3.4 |
| NG/after shampooing | C2 + A + H₂O₂ | 38.2 | 5.0 | −1.0 | |
| PG/before shampooing | C2 + A + H₂O₂ | 35.0 | 2.8 | 1.5 | 2.1 |
| PG/after shampooing | C2 + A + H₂O₂ | 35.5 | 3.8 | −0.3 | |
| NG/before shampooing | C3 + A + H₂O₂ | 36.6 | 3.0 | 1.6 | 3.1 |
| NG/after shampooing | C3 + A + H₂O₂ | 38.3 | 4.2 | −0.5 | |
| PG/before shampooing | C3 + A + H₂O₂ | 34.6 | 2.5 | 1.8 | 1.6 |
| PG/after shampooing | C3 + A + H₂O₂ | 34.9 | 2.5 | 0.3 | |
| NG/before shampooing | C4 + A + H₂O₂ | 36.3 | 3.4 | 1.6 | 2.0 |
| NG/after shampooing | C4 + A + H₂O₂ | 37.8 | 4.0 | 0.4 | |
| PG/before shampooing | C4 + A + H₂O₂ | 33.7 | 1.7 | 2.3 | 2.3 |
| PG/after shampooing | C4 + A + H₂O₂ | 35.3 | 2.5 | 0.9 | |
| NG/before shampooing | C5 + A + H₂O₂ | 37.1 | 3.4 | −0.4 | 3.3 |
| NG/after shampooing | C5 + A + H₂O₂ | 40.2 | 3.9 | −1.1 | |
| PG/before shampooing | C5 + A + H₂O₂ | 34.5 | 3.2 | 0.5 | 2.3 |
| PG/after shampooing | C5 + A + H₂O₂ | 36.3 | 3.2 | −0.9 | |

These results show that the lightening compositions of the invention show very good shampoo fastness and also little selectivity between natural hair and permanent-waved hair.

The invention claimed is:

1. A dye composition comprising, in a suitable dyeing medium, at least one oxidizing agent, at least one alkaline agent present in the composition in an amount such that the pH of the composition is greater than 7, and at least one cationic mixed direct dye, said at least one cationic mixed direct dye comprising at least two different chromophores linked together via a linker, wherein said at least two different chromophores exhibit at least one absorption maximum between 400 and 800 nm.

2. The composition of claim 1, wherein said at least two different chromophores are chosen from acridine, acridone, anthranthrone, anthrapyrimidine, anthraquinone, azine, azo, azomethine, benzanthrone, benzimidazole, benzimidazolone, benzindole, benzoxazole, benzopyran, benzothiazole, benzoquinone, bis-azine, bis-isoindoline, carboxanilide, coumarin, cyanins, diazine, diketopyrrolopyrrole, dioxazine, diphenylamine, diphenylmethane and dithiazine chromophores, flavonoids, fluorindines, formazans, hydrazones, hydroxy ketones, indamines, indanthrones, indigoids, pseudo-indigoids, indophenols, indoanilines, isoindolines, isoindolines, isoindolinones, isoviolanthrones, lactones, methines, naphthalimides, naphthanilides, naphtholactams, naphthoquinones, nitro dyes, oxadiazoles, oxazines, perilones, perinones, perylenes, phenazines, phenothiazines, phthalocyanin, polyenes/carotenoids, porphyrins, pyranthrones, pyrazolanthrones, pyrazolones, pyrimidinoanthrones, pyronines, quinacridones, quinolines, quinophthalones, squaranes, stilbenes, tetrazoliums, thiazines, thioindigo, thiopyronines, triarylmethanes, and xanthenes.

3. The composition of claim 2, wherein said cyanins are chosen from azacarbocyanin, diazacarbocyanin, diazahemicyanin, hemicyanin and tetraazacarbocyanin.

4. The composition of claim 2, wherein said flavonids are chosen from flavanthrones and flavones.

5. The composition of claim 2, wherein said hydrazones are chosen from aryihydrazones.

6. The composition of claim 2, wherein said nitro dyes are chosen from nitro(hetero)aromatic dyes.

7. The composition of claim 2, wherein said at least two different chromophores are chosen from acridine, acridone, anthranthrone, anthraquinone, azine, azo, azomethine, benzanthrone, benzoquinone, bis-azine, cyanins, diazine, diketopyrrolopyrrole, dioxazine, diphenylmethane, dithiazine, flavonoids, formazans, hydrazones, indamines, indanthrones, indigoids, pseudo-indigoids, indophenols, indoanilines, isoviolanthrones, methines, naphthalimides, naphtholactams, naphthoquinones, nitro dyes, phenazines, phenothiazines, phthalocyanin, polyenes/carotenoids, porphyrins, pyrazolones, quinacridones, quinophthalones, stilbenes, tetrazoliums, thiazines, thioindigo, thiopyronines, triarylmethanes, and xanthenes.

8. The composition of claim 7, wherein said cyanins are chosen from azacarbocyanin, diazacarbocyanin, diazahemicyanin, hemicyanin and tetraazacarbocyanin.

9. The composition of claim 7, wherein said flavonoids are chosen from flavanthrones and flavones.

10. The composition of claim 7, wherein said hydrazones are chosen from aryihydrazones.

11. The composition of claim 7, wherein said nitro dyes are chosen from nitro(hetero)aromatic dyes.

12. The composition of claim 2, wherein said at least two different chromophores are chosen from azo, xanthene, hydrazone and arylhydrazone, phenothiazine, acridine, diketopyrrolopyrrole, cyanin, anthraquinone, methine, azomethine, indigoid and nitro chromophores.

13. The composition of claim 12, wherein said cyanin chromophore is tetraazacarbocyanin.

14. The composition of claim 12, wherein said nitro chromophore is a nitro(hetero)aromatic chromophore.

15. The composition of claim 1, wherein said at least one mixed direct dye is dicationic.

16. The composition of claim 12, wherein said at least one mixed direct dye comprises two or three different chromophores, wherein at least two of said two or three chromophores are cationic, and said linker is cationic or non-cationic.

17. The composition of claim 1, wherein the at least one mixed direct dye corresponds to the formula Dye 1-L-Dye 2, wherein L is a cationic or non-cationic linker and Dye 1 and Dye 2 are different cationic chromophores.

18. The composition of claim 1, wherein at least one of the at least two chromophores is a cationic chromophore comprising a quaternized nitrogen atom.

19. The composition of claim 1, wherein the at least one mixed direct dye comprises at least one cationic azo chromophore.

20. The composition of claim 1, wherein the linker is chosen from an optionally substituted, $C_1$–$C_{20}$ linear, branched or cyclic hydrocarbon-based chain, wherein: at least one of the carbon atoms of the chain is optionally replaced with at least one hetero atom and/or with at least one group comprising a hetero atom and; the hydrocarbon-based chain is optionally unsaturated or comprises at least one optionally substituted radical chosen from alkylene radicals, arylene radicals, divalent terephthalamide radicals, divalent heterocyclic radicals, and —NH—CO— radicals.

21. The composition of claim 1, wherein said linker comprises an atom or a group of atoms that isolate each of said at least two chromophores comprised in the at least one mixed dye such that the absorption maxima of said at least two chromophores, as comprised in the at least one mixed dye, are not modified by more than 30 nanometers, relative to the absorption maxima of each of said at least two chromophores measured separately.

22. The composition of claim 1, wherein the at least one mixed direct dye is chosen from those of formula:

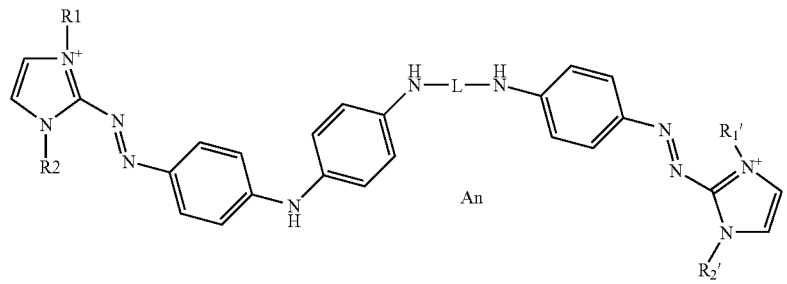

wherein

L is a linker;

R1 and R1', which may be the same or different, are chosen from alkyl radicals optionally substituted with at least one radical chosen from hydroxyl, $C_1$–$C_2$ alkoxy, $C_2$–$C_4$ (poly)hydroxyalkoxy, amino, $C_1$–$C_2$ (di)alkylamino and optionally substituted aryl radicals;

R2 and R2', which may be the same or different, are chosen from alkyl radicals, optionally substituted with at least one radical chosen from hydroxyl, $C_1$–$C_2$ alkoxy, $C_2$–$C_4$ (poly)hydroxyalkoxy, amino and $C_1$–$C_2$ (di)alkylamino radicals; and optionally substituted phenyl radicals; and An is at least one, identical or different, monovalent or multivalent anion.

23. The composition of claim 22, wherein said alkyl radicals are $C_1$–$C_6$ alkyl radicals.

24. The composition of claim 21, wherein the at least one mixed direct dye is chosen from the following structures:
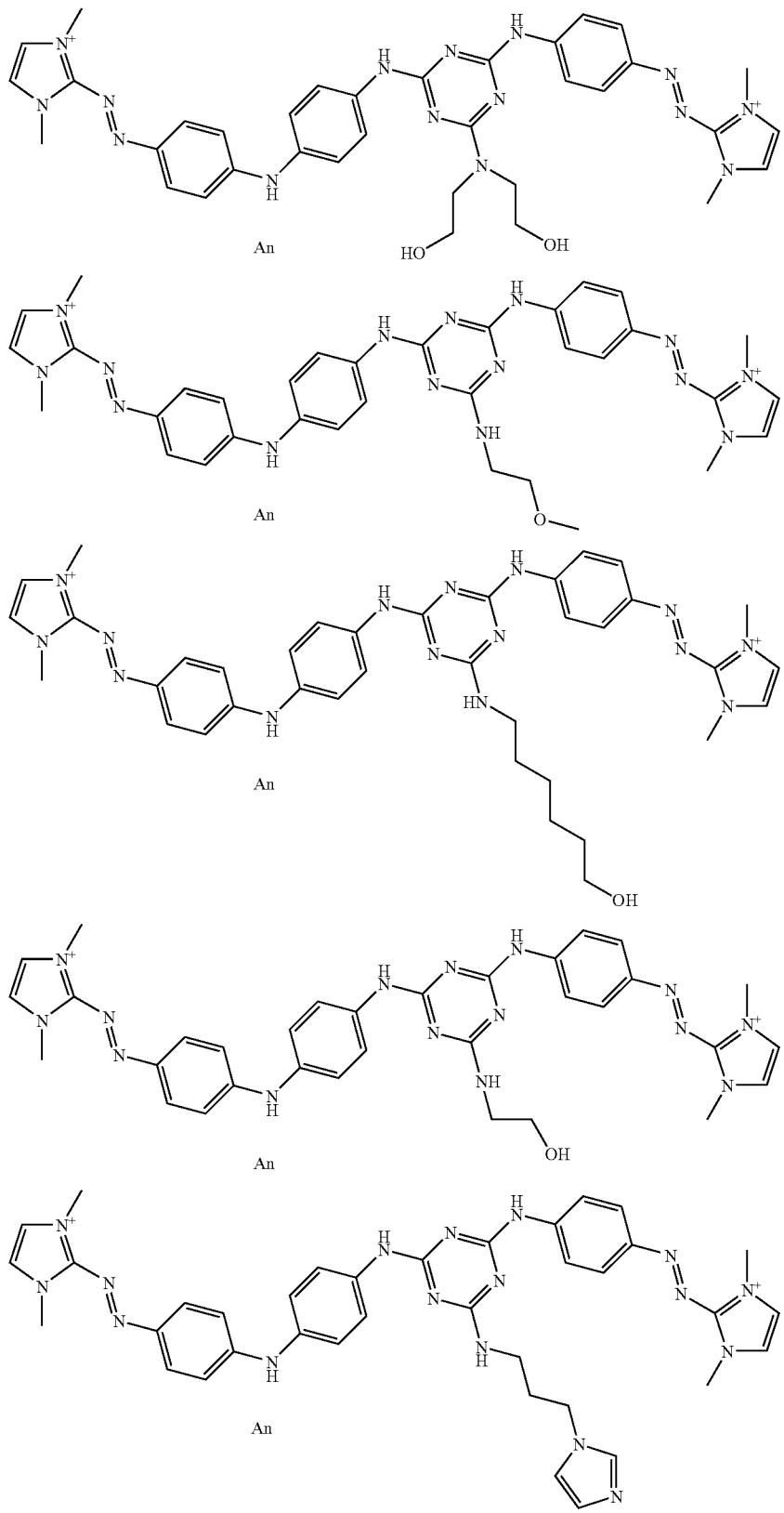

-continued

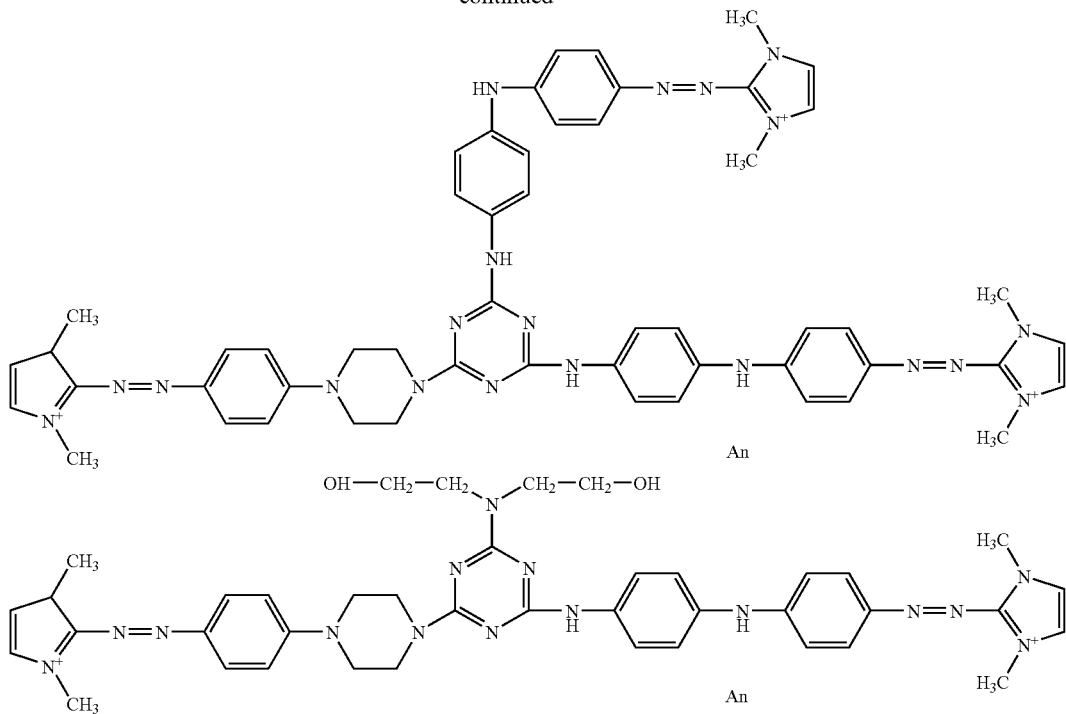

wherein An represents at least one anion chosen from identical and different, monovalent and multivalent anions.

25. The composition of claim 22, wherein the at least one anion An is an organic or mineral anion chosen from halides, hydroxides, sulfates, hydrogen sulfates, $(C_1-C_6)$alkyl sulfates, phosphates, carbonates, hydrogen carbonates, perchlorates, acetates, tartrates, citrates, oxalates, $(C_1-C_6)$alkylsulfonates, and arylsulfonates optionally substituted with a $C_1-C_4$ alkyl radical.

26. The composition of claim 1, wherein the at least one mixed direct dye is present in the composition in an amount ranging from 0.001% to 20% by weight, relative to the total weight of the composition.

27. The composition of claim 1, wherein the at least one mixed direct dye is present in the composition in an amount ranging from 0.01% to 5% by weight, relative to the total weight of the composition.

28. The composition of claim 1, further comprising at least one direct dyes other than said at least one mixed direct dye.

29. The composition of claim 1, further comprising at least one oxidation base chosen from para-phenylenediamines, bis(phenyl)alkylenediamines, para-aminophenols, ortho-aminophenols, heterocyclic bases, and the addition salts thereof.

30. The composition of claim 1, further comprising at least one coupler chosen from meta-phenylenediamines, meta-aminophenols, meta-diphenols, naphthalene-based couplers, heterocyclic couplers, and the addition salts thereof.

31. The composition of claim 29, wherein said at least one oxidation base is present in the composition in an amount ranging from 0.001% to 10% by weight, relative to the total weight of the dye composition.

32. The composition of claim 30, wherein said at least one coupler is present in the composition in an amount ranging from 0.001% to 10% by weight, relative to the total weight of the dye composition.

33. The composition of claim 1, wherein the composition has a pH ranging from 8 to 11.

34. The composition of claim 1, wherein the at least one alkaline agent is chosen from aqueous ammonia, alkaline carbonates, alkanolamines, sodium hydroxide, potassium hydroxide and the compounds of formula (II):

in which W is a propylene residue that is unsubstituted or substituted with a hydroxyl group or a $C_1-C_4$ alkyl radical; and $R_a$, $R_b$, $R_c$ and $R_d$, which may be identical or different, are chosen from hydrogen atoms, $C_1-C_4$ alkyl radicals and $C_1-C_4$ hydroxyalkyl radicals.

35. The composition of claim 34, wherein said alkanolamines are chosen from monoethanolamine, diethanolamine, triethanolamine, and derivatives thereof.

36. The composition of claim 1, wherein said at least one oxidizing agent is hydrogen peroxide.

37. A process for the oxidation dyeing of keratin fibers, comprising:
applying to said keratin fibers a dye composition comprising, in a suitable dyeing medium, at least one oxidizing agent, at least one alkaline agent in an amount such that the pH of the composition is greater than 7, and at least one cationic mixed direct dye, said cationic mixed direct dye comprising at least two different chromophores that are linked together via a linker and exhibit at least one absorption maximum between 400 and 800 nm; and wherein said dye composition is left on said keratin fibers for a period of time that is sufficient to develop a desired coloration.

38. The process of claim 37, wherein said at least one oxidizing agent is comprised in a composition different from the one comprising the mixed dye.

39. A multi-compartment kit comprising:
at least one first compartment comprising a dye composition comprising, in a suitable dyeing medium, at least one alkaline agent in an amount such that the pH of the composition is greater than 7, and at least one cationic mixed direct dye, wherein said cationic mixed direct dye comprises at least two different chromophores linked together via a linker, wherein said at least two chromophores exhibit at least one absorption maximum between 400 and 800 nm; and at least one second compartment comprising at least one oxidizing agent.

* * * * *

UNITED STATES PATENT AND TRADEMARK OFFICE
CERTIFICATE OF CORRECTION

PATENT NO.         : 7,172,633 B2
APPLICATION NO. : 10/980899
DATED                 : February 6, 2007
INVENTOR(S)       : Henri Samain et al.

It is certified that error appears in the above-identified patent and that said Letters Patent is hereby corrected as shown below:

In claim 4, column 29, line 11, "flavonids" should read --flavonoids--.

In claim 5, column 29, line 14, "aryihydrazones." should read --arylhydrazones.--.

In claim 10, column 29, line 51, "aryihydrazones." should read --arylhydrazones.--.

In claim 25, column 33, lines 37-38, "perchiorates," should read --perchlorates,--.

In claim 28, column 33, line 51, "dyes" should read --dye--.

In claim 33, column 34, line 37, "8to 11." should read --8 to 11.--.

Signed and Sealed this

First Day of May, 2007

JON W. DUDAS
*Director of the United States Patent and Trademark Office*